United States Patent
Levy

(10) Patent No.: US 11,471,334 B2
(45) Date of Patent: Oct. 18, 2022

(54) TWO LAYER BANDAGE

(71) Applicant: Peter L. Levy, San Francisco, CA (US)

(72) Inventor: Peter L. Levy, San Francisco, CA (US)

( * ) Notice: Subject to any disclaimer, the term of this patent is extended or adjusted under 35 U.S.C. 154(b) by 316 days.

(21) Appl. No.: 16/899,718

(22) Filed: Jun. 12, 2020

(65) Prior Publication Data
US 2021/0386593 A1 Dec. 16, 2021

(51) Int. Cl.
*A61F 13/02* (2006.01)
*A61F 13/00* (2006.01)

(52) U.S. Cl.
CPC ............. *A61F 13/0206* (2013.01); *A61F 2013/00863* (2013.01); *A61F 2013/00889* (2013.01)

(58) Field of Classification Search
CPC ........ A61F 13/0206; A61F 2013/00863; A61F 2013/00889; A61F 13/0203; A61F 13/0226

See application file for complete search history.

(56) References Cited

U.S. PATENT DOCUMENTS

| | | | | | |
|---|---|---|---|---|---|
| 2,722,220 | A | * | 11/1955 | Mestrand | A61F 13/0203 606/215 |
| 4,909,243 | A | * | 3/1990 | Frank | A61F 13/0203 604/304 |
| 5,086,763 | A | * | 2/1992 | Hathman | A61F 13/0246 602/42 |
| 5,556,375 | A | * | 9/1996 | Ewall | A61F 13/0203 602/54 |
| 5,607,388 | A | * | 3/1997 | Ewall | A61F 13/023 604/304 |
| 5,702,356 | A | * | 12/1997 | Hathman | A61F 13/0206 602/41 |
| 6,043,408 | A | * | 3/2000 | Geng | A61F 13/023 602/57 |
| 2011/0015557 | A1 | * | 1/2011 | Aali | A61F 13/00068 602/56 |

\* cited by examiner

*Primary Examiner* — Camtu T Nguyen
(74) *Attorney, Agent, or Firm* — Walt Froloff

(57) ABSTRACT

A two layer bandage with a hole or opening larger than the wound area for a first layer in contact with the skin is shown and a second layer which carries an absorbent portion cover wound just above the open portion of the first layer. The absorbent is imbedded or attached in the body of the second layer such that the absorbent portion of the bandage can be replaced without disturbing the wound.

4 Claims, 5 Drawing Sheets

TWO LAYER BANDAGE

BACKGROUND

Field of the Invention

The present invention relates generally to improvements in the common consumer item bandage. More particularly, the invention relates to an improved form of bandage which allows for changing without wound re-injury, new pain or infection.

Background of the Invention

Bandages come in many forms and products. A base member of an adhesive type bandages typically include a pad of gauze or similar absorbent material positioned at a center of a strip of adhesive tape. When applied, the pad is positioned over a wound and secured to the skin via the adhesive tape.

There are many bandages in the market place, for example liquid skin bandages, extra thick cushioning pad, tough cloth tape, water proof, water resistant and more. The primary purpose of a adhesive bandage is to slow and stop bleeding from an injury. At times the concern is to stop or prevent bleeding at an acute stage of the injury.

However, there is a need for bleeding cessation to be reasonably comfortable as pain is generally occurring and especially where there is no significant bleeding. However, bleeding is an important aspect of wound healing, as the blood washes the injury with lymphatic fluid and immune system antigens and white blood cells, as well as with coagulant to form a scab to promote protection from infection and healing from within the epidermis.

Furthermore some methods of bandages allow pressure in the injury side to occur in a case of bleeding while other methods require a periodic change of bandage providing fresh gauze or absorbent. When changing out the bandage, an aggressive skin adhesive maintaining it's grip on the bandaged area can reopen the wound causing fresh bleeding and potential infection.

What is needed are bandages that can stop bleeding, yet allow natural bleeding and healing without potential for reopening the wound during bandage replacement.

SUMMARY

The present invention discloses a two layer bandage with an absorbent refresh layer. A two layer bandage having a first and second layer each having two sides. The first layer has a first side having strong skin adhesion properties for adhering a bandage to tissue and a second side for adhesion character with minimal adhesion properties commensurate with mating with a second layer. The first layer has an opening with a shape within its perimeter compliant with the first layer adhering to the wound area centerline and folding skin surrounding a wound into wound to the extent possible while providing blood and fluid flow out from the unclosed skin portion of the wound. A second layer with two sides is disclosed with a first side having adhesive surface with adhesion commensurate with removal of the second layer without disturbing the first layer, and a region with absorbent pad or gauze for configuring and positioning the pad over the first layer opening facing the wound for absorbing any blood effluent transporting through the first layer opening boundary. The second layer has a tab coupled to an end edge of the second layer for removing the second layer containing the absorbent pad and without disturbing the first layer or the wound, whereby the removal and replacement of the second layer bandage replaces a used pad without residual adhesion to the wound region or the first layer adhesive part of the bandage to skin layer region.

BRIEF DESCRIPTION OF DRAWINGS

Specific embodiments of the invention will be described in detail with reference to the following figures.

DETAILED DESCRIPTION

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Objects and Advantages

An object of the invention is to provide a bandage where removing and replacing does not irritate the skin.

Another object of the invention is for creating a bandage where removing and replacing dressings does not reopen wound or scab and causes bleeding to re-occur.

Yet another objective of the invention is to provide a bandage that reduces the cost of replacement by replacing only a component part.

Another object of the invention is to provide a bandage pull tab for easy and pain-free replacement.

Yet another object of the invention is to create a bandage where multiple replacement dressings reduce the chances of infection or further inflammation.

Figure 1:
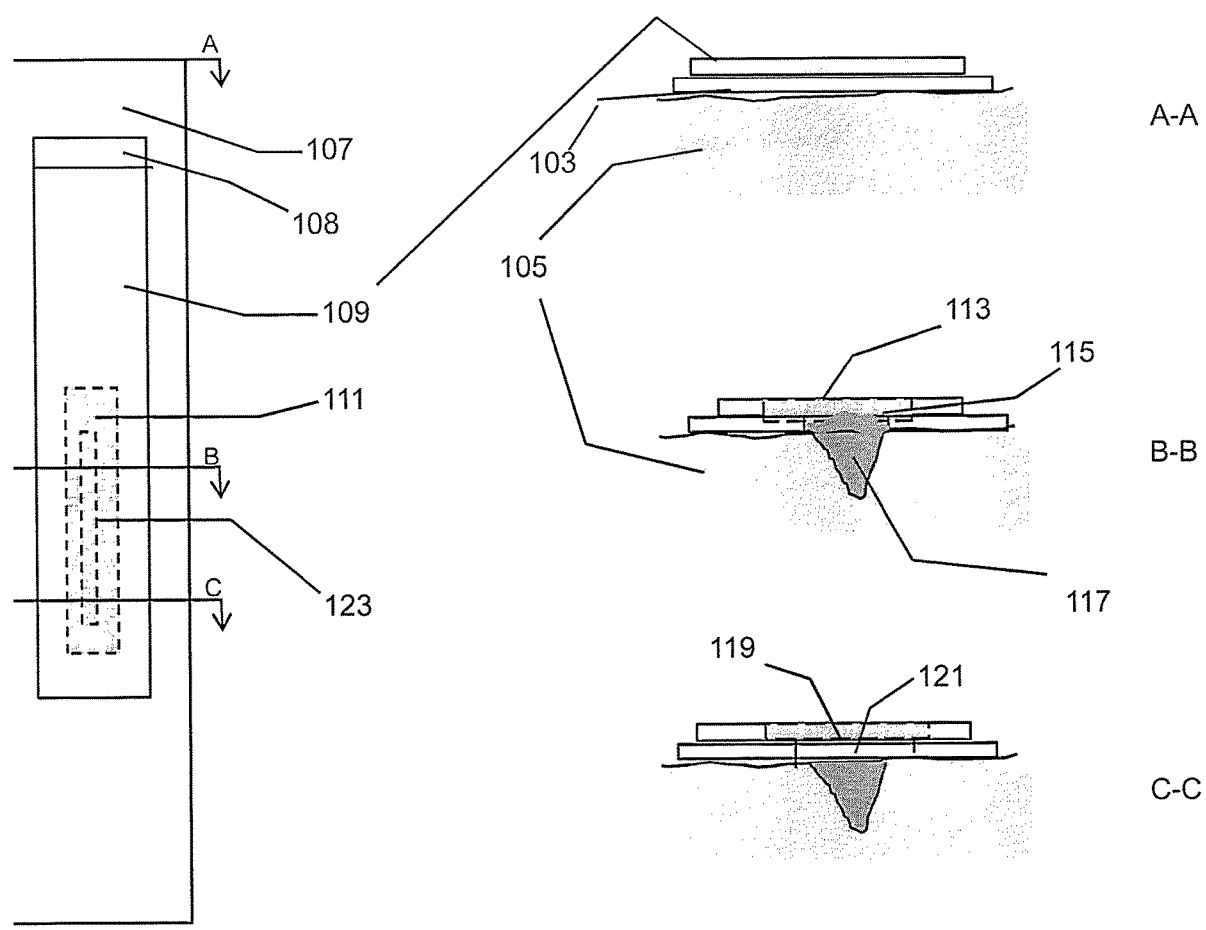
FIG. 1 illustrates a front and cross-section views of a two layer bandage with a top disposable layer in an embodiment of the invention

The present invention discloses several embodiments for making a two layer or two strip adhesive bandage for easy maintenance FIG. 1 illustrates a front and cross-section views of a two layer bandage with a top easy renewable changeable absorbing layer in an embodiment of the invention.

In an embodiment of the invention a two layer 107 111 bandage with a hole or opening 123 115 121 that is larger than the wound area 117 for a first layer 107 and having adhesive on the underside side 103 in contact with the skin 105 is shown. A second layer 109 113 of the bandage carries an absorbent portion 111 113 to cover wound and is attached to a bandage first layer 103 107 with its adhesive side flush with the first layer 103 107 and the second layer 109 absorbent 111 completely covering the opening 123 in the first layer 107. The absorbent 109 111 is imbedded or attached in the body of the second bandage layer 109 113 119. In an embodiment of the invention the second bandage layer 109 can be shorter in length than the first layer 107, has adhesive at the side to attach to the first layer 107 and has a pull tab 108 across one end of the second layer 109 with no adhesive on the tab to enable easy removal of the second layer without disturbing the first layer of the bandage. The pull tab 108 can also be at the corner of the second layer 109.

Figure 2:
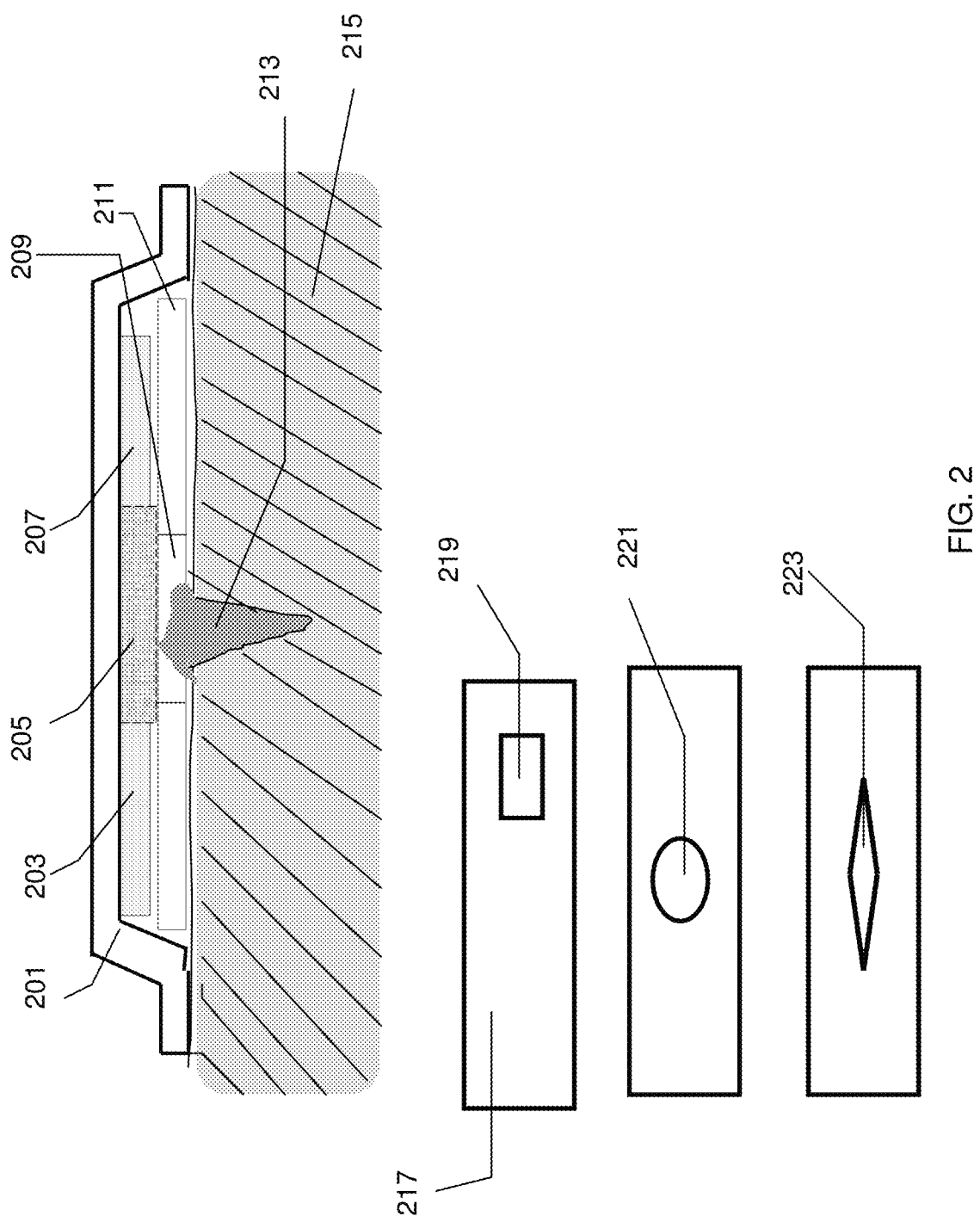
FIG. 2 shows a cross-section view of a two layer bandage with a top disposable layer and first layer opening shapes in an embodiment of the invention.

FIG. 2 shows a cross-section view of a two layer bandage with a top disposable layer and first layer opening shapes in an embodiment of the invention.

In an embodiment of the invention a two layer adhesive bandage with absorbent refresh layer is shown having a two layer bandage having a first 211 and second layer 201 each having two sides or surfaces. A first layer 211 has a first side having strong skin adhesion properties for adhering a bandage to skin 215 and a second side for adhesion with minimal adhesion properties, adhesion commensurate with mating with a second layer 201. The first layer has an opening 209 with a shape having a perimeter containing a wound 213 with the first layer adhering to the wound 213 area while holding the skin surrounding a wound 213 into wound to the extent possible with adhesion. This minimizes bleeding and fluid flow out from the unclosed skin portion of the wound 213 by reducing the blood outflow area and the blood clotting or scab formation area. The first layer opening shape perimeter can come in the form of any closed polygon.

A second layer 201 of the bandage has two sides, a first side has an adhesive surface 201 203 with adhesion commensurate with removal of the second layer 201 from the first layer 211 without disturbing the first layer's 211 position over or touching the wound 213 repairing, and a region with absorbent 205 pad, hole array or gauze configured for positioning the absorbent 205 over the first layer 211 opening 209 facing the wound 213 for absorbing any blood effluent transporting through the first layer 211 opening boundary. The second layer 201 can have a tab coupled to an end edge of the second layer 201 for removing the second layer used absorbent 205 with the blood/fluid absorbent pad without disturbing the first layer or the wound 213. The removal and replacement of the second layer 210 bandage replaces a saturated pad 205 without residual adhesion to the wound region 215 or the first layer 211 adhesive part of the bandage to skin layer region 215.

In an aspect of the invention the first layer openings 219 221 223 can have perimeter shapes more or less in the shape for containing a wound surface opening for holding down any wound opening tear skin to minimize blood outflow area, the perimeter shape be it more or less rectangular 219, round 221, diamond 223 or other shapes. The openings 219 221 223 will be integral to a first layer 217 which has an adhesive side adjacent to the skin for staying firmly in position through a healing period, and allowing for a second disposable layer to be refreshed on demand.

In some embodiments of the invention, a first layer opening will have a polygonal shape perimeter with polygon shape more or less centerline with an axis of the bandage orientable on the skin cut or opening for best coverage of the cut.

Figure 3:
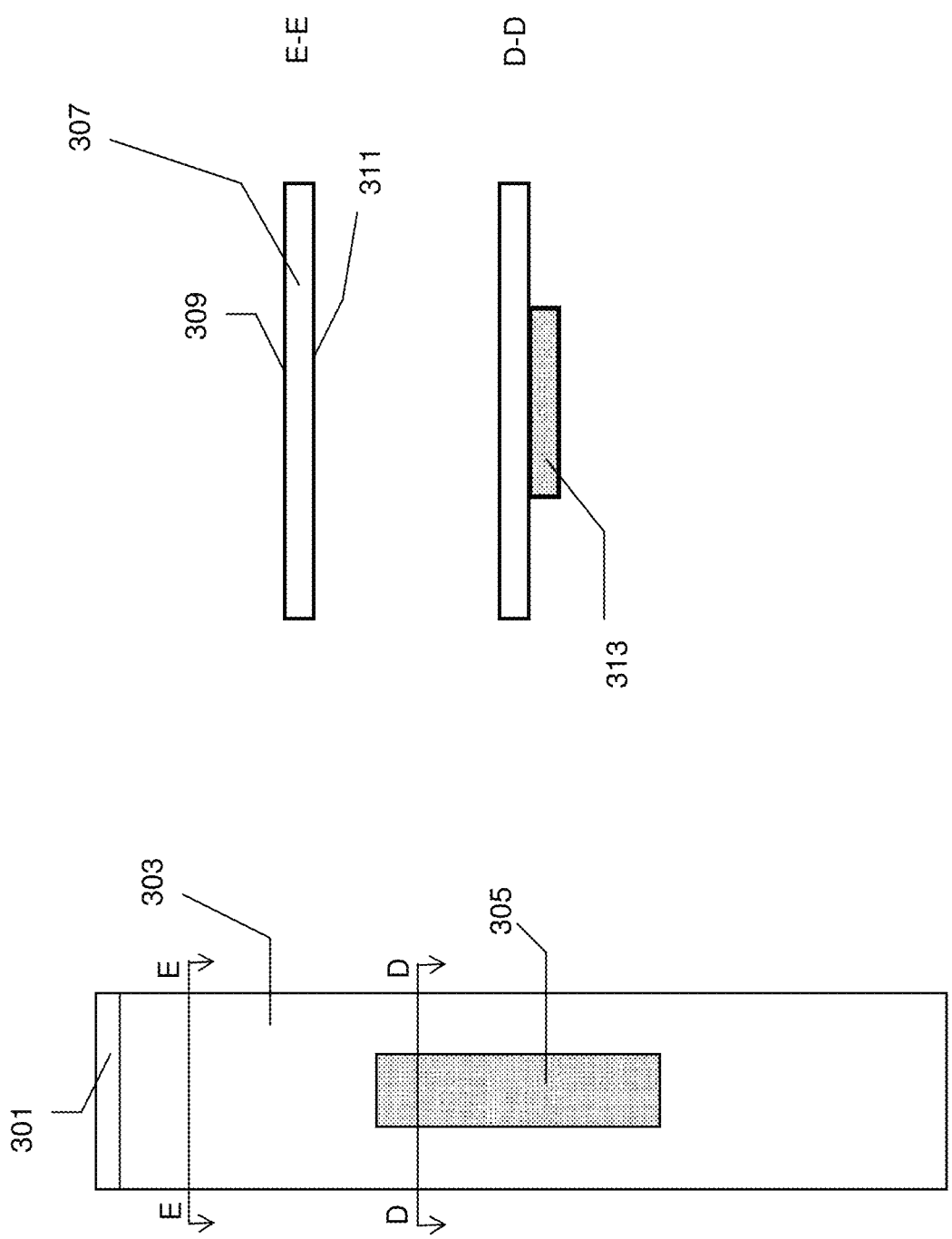
FIG. 3 displays second layer disposable component in a aspect of the invention.

FIG. 3 displays second layer disposable component in a aspect of the invention. A second layer 303 of a two layer bandage is shown with second layer side one 311 having region with absorbent 305 313 from sterile absorbent material of padding, cotton, gauze, layered gauze or bio-chemically treated. The second layer 303 side one will have and adhesive with weaker holding power than the adhesive on layer one skin adjacent side. The second layer 303 307 may have a tab 301 with non-adhesive surface for easy layer two removal. In another embodiment the second layer 303 will have a side two 309 having a waterproof and or water repellent surface.

Figure 4:
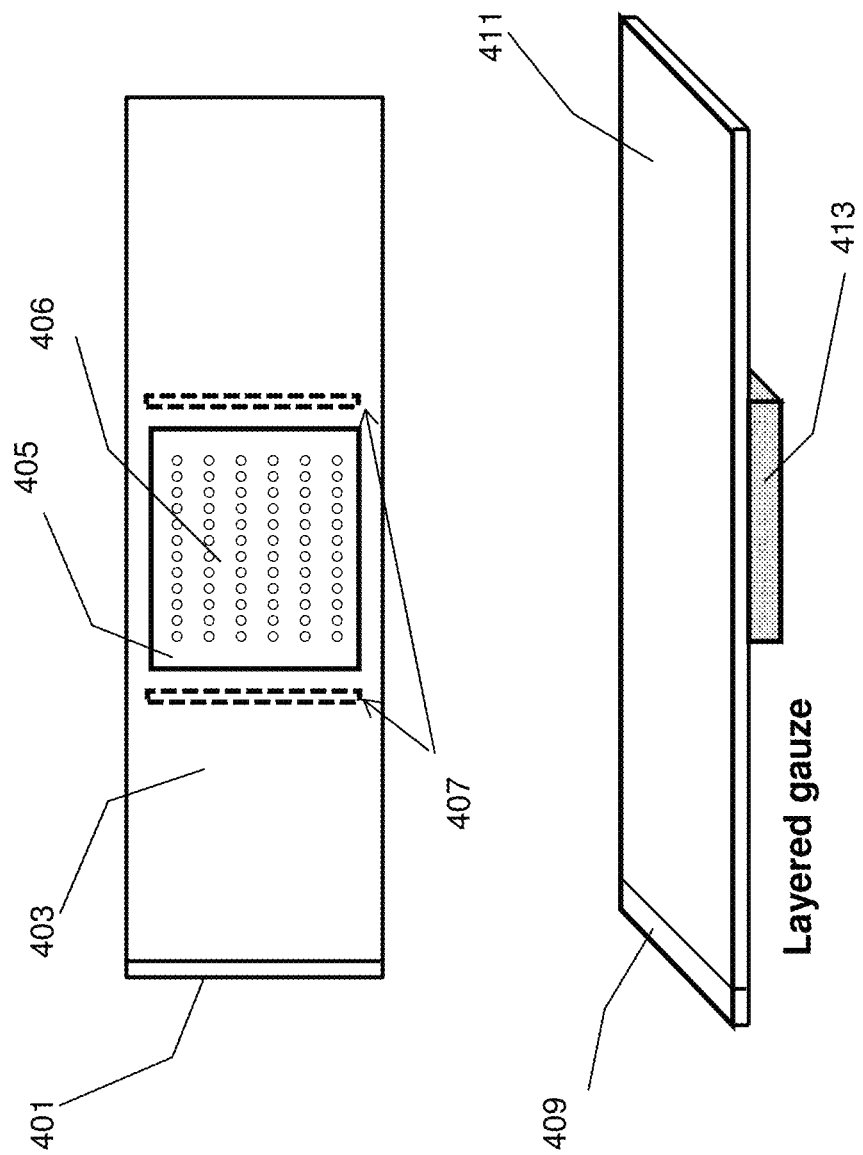
FIG. 4 shows front and lateral views of second layer with disposable absorbents in an embodiment of the invention

FIG. 4 shows front and lateral views of second layer with disposable absorbents in an embodiment of the invention A two layer bandage is shown having a second layer 403 411 construction having a sterile array of ventilation holes 406 on a small protrusion 407 elevating the pad region 405 from the wound to promote drying while healing in a sterile air environment with dirt on wound aggregation prevention by physical barrier. The second layer region side nearest the first layer but not including the pad region 405 has an adhesive surface snuggly coupled with the first layer opposite to the skin side and facing the second layer, with adhesion properties of the second layer weaker than the first layer skin side adhesion. In another embodiment a pull tab 401 409 is edge coupled for non-sticky ease of removal for refresh of absorbent pad 413 which is embedded or coupled to the second layer 411 403.

Figure 5:
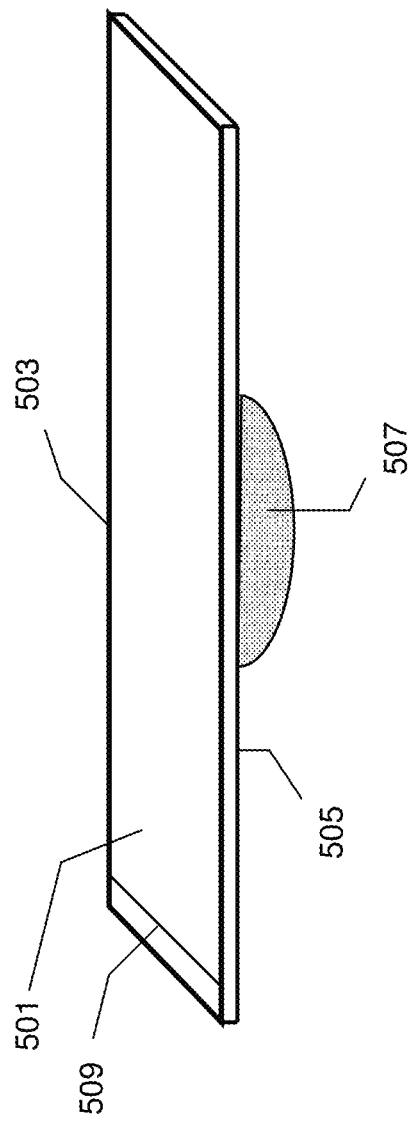
FIG. 5 illustrates a second layer of a bandage with compressible gauze in an embodiment of the invention

FIG. 5 illustrates a second layer of a bandage with compressible gauze in an embodiment of the invention. A two layer bandage showing a second layer 501 having a water proof and or water repellant side one 503 and an adhesive side two 505, the adhesive side one in the non-absorbent pad 507 area for coupling snuggly to a first layer. The absorbent 507 can be compressible gauze for application of pressure on a wound to slow/stop bleeding. Other pad materials can be non-sterile medicant treated to stop bleeding and promote healing. The second layer has a pull tab 509 on one edge of the second layer 501 without adhesive surface.

Therefore, while the invention has been described with respect to a limited number of embodiments, those skilled in the art, having benefit of this invention, will appreciate that other embodiments can be devised which do not depart from the scope of the invention as disclosed herein. Other aspects of the invention will be apparent from the following description and the appended claims.

What is claimed is:

1. A two layer bandage comprising:
   a first layer comprises a first side and a second side opposite the first side, the first side having a first adhesive adapted to adhering the first layer to skin and the second side having a second adhesive;
   the first layer further having an opening adapted to surround a wound and constrain bodily exudates therewithin;
   a second layer, comprises a first side and a second side, the first side having third adhesive releasably coupled with the second adhesive so as to allow for removal of the second layer from the first layer without disturbing the first layer, and the second layer carries an absorbent material on the first side, wherein the absorbent material is placed over the opening in the first layer;
   the second layer comprises an array of ventilation holes and protrusions, wherein the protrusions elevate the absorbent material so as to create a gap between the wound and the absorbent material to promote healing;
   the second layer further comprises a tab coupled to an end edge of the second layer for removing the second layer and the absorbent material without disturbing the first layer.

2. The two layer bandage of claim 1, wherein the opening in the first layer has a perimeter of any closed polygon.

3. The two layer bandage of claim 1, wherein the absorbent material comprises a gauze.

4. The two layer bandage of claim 1, wherein the second layer comprises a water-proof material.

\* \* \* \* \*